United States Patent
Van Bolhuis et al.

(10) Patent No.: US 7,734,346 B2
(45) Date of Patent: Jun. 8, 2010

(54) IDENTIFICATION OF PREMATURE ATRIAL CONTRACTIONS THAT TRIGGER ARRHYTHMIA

(75) Inventors: Harm H. Van Bolhuis, Warmond (NL); Willem Stegnik, Laren (NL); Henk Westendorp, Zutphen (NL)

(73) Assignee: Medtronic, Inc., Minneapolis, MN (US)

( * ) Notice: Subject to any disclaimer, the term of this patent is extended or adjusted under 35 U.S.C. 154(b) by 452 days.

(21) Appl. No.: 10/424,580

(22) Filed: Apr. 25, 2003

(65) Prior Publication Data
US 2004/0215273 A1 Oct. 28, 2004

(51) Int. Cl.
*A61N 1/36* (2006.01)

(52) U.S. Cl. .............................. 607/9; 607/14

(58) Field of Classification Search ............... 607/5–32; 600/508–510, 518, 515
See application file for complete search history.

(56) References Cited

U.S. PATENT DOCUMENTS

| | | | | |
|---|---|---|---|---|
| 5,243,976 | A * | 9/1993 | Ferek-Petric et al. | 607/6 |
| 5,316,001 | A * | 5/1994 | Ferek-Petric et al. | 600/454 |
| 5,683,429 | A * | 11/1997 | Mehra | 607/14 |
| 5,782,887 | A * | 7/1998 | van Krieken et al. | 607/25 |
| 5,871,507 | A | 2/1999 | Obel et al. | |
| 5,978,709 | A | 11/1999 | Begemann et al. | |
| 6,029,087 | A | 2/2000 | Wohlgemuth | |
| 6,058,328 | A * | 5/2000 | Levine et al. | 607/14 |
| 6,185,459 | B1 * | 2/2001 | Mehra et al. | 607/14 |
| 6,205,357 | B1 * | 3/2001 | Ideker et al. | 607/14 |
| 6,266,554 | B1 * | 7/2001 | Hsu et al. | 600/515 |
| 6,377,852 | B1 * | 4/2002 | Bornzin et al. | 607/9 |
| 6,708,062 | B2 * | 3/2004 | Ericksen et al. | 607/9 |
| 6,731,983 | B2 * | 5/2004 | Ericksen et al. | 607/14 |
| 6,754,525 | B1 * | 6/2004 | Province et al. | 607/4 |
| 6,865,414 | B1 * | 3/2005 | Levine | 600/510 |
| 6,944,495 | B2 * | 9/2005 | MacAdam et al. | 600/521 |
| 7,035,684 | B2 * | 4/2006 | Lee | 600/513 |
| 7,181,277 | B1 * | 2/2007 | Shelchuk et al. | 607/9 |
| 7,181,282 | B1 * | 2/2007 | Province et al. | 607/17 |
| 2001/0014817 | A1 | 8/2001 | Armstrong et al. | 607/14 |
| 2002/0183636 | A1 * | 12/2002 | Struble | 600/510 |
| 2003/0032986 | A1 * | 2/2003 | Kupper | 607/5 |
| 2003/0036773 | A1 * | 2/2003 | Whitehurst et al. | 607/3 |
| 2003/0036777 | A1 | 2/2003 | Sheth et al. | 607/9 |
| 2003/0083701 | A1 * | 5/2003 | Ericksen et al. | 607/9 |
| 2003/0083705 | A1 * | 5/2003 | Ericksen et al. | 607/14 |
| 2003/0120165 | A1 * | 6/2003 | Bjorling | 600/515 |
| 2003/0144701 | A1 * | 7/2003 | Mehra et al. | 607/17 |
| 2004/0162590 | A1 * | 8/2004 | Whitehurst et al. | 607/17 |
| 2004/0167416 | A1 * | 8/2004 | Lee | 600/513 |

FOREIGN PATENT DOCUMENTS

| | | |
|---|---|---|
| EP | 0 547 734 A2 | 6/1993 |
| EP | 0965 361 A2 | 12/1999 |

* cited by examiner

*Primary Examiner*—Carl H Layno
*Assistant Examiner*—Joseph Stoklosa
(74) *Attorney, Agent, or Firm*—Stephen W. Bauer (57) ABSTRACT

In general, the invention is directed to techniques for delivery of pacing in response to a premature atrial contraction (PAC) to prevent atrial arrhythmia, i.e., delivery of post-PAC pacing pulses. The techniques may involve monitoring the success rate of prior post-PAC pacing sequences, and adjusting the number of post-PAC pacing pulses delivered subsequent post-PAC pacing sequences based on a success rate. In addition, the techniques may involve adjusting the post-PAC pacing interval based on the success rate.

12 Claims, 6 Drawing Sheets

IDENTIFICATION OF PREMATURE ATRIAL CONTRACTIONS THAT TRIGGER ARRHYTHMIA

TECHNICAL FIELD

The invention relates to implantable medical devices and, more particularly, to cardiac pacemakers that deliver pacing pulses in response to detection of premature atrial contractions.

BACKGROUND

Tachyarrhythmias are episodes of high-rate cardiac depolarizations. Tachyarrhythmias may occur in one chamber of the heart or may be propagated from one chamber to another. Some tachyarrhythmias are sufficiently high in rate to compromise cardiac output from the chamber affected, leading to loss of consciousness or death in the case of ventricular fibrillation, or weakness and dizziness in the case of atrial fibrillation. Atrial fibrillation is often debilitating, due to the loss of atrial cardiac output, and may sometimes lead to ventricular fibrillation.

Fibrillation may be terminated by administering high energy level cardioversion or defibrillation shocks until the fibrillation is terminated. For example, an implanted device may deliver defibrillation shocks via an electrode carried by a lead implanted within the heart. Unfortunately, the high energy levels associated with cardioversion/defibrillation shocks can cause significant pain to the patient. In addition, atrial defibrillation shocks can sometimes give rise to ventricular arrhythmias. Therefore, it is generally desirable to avoid the onset of atrial fibrillation, and the need to apply defibrillation shocks.

Some implanted devices deliver anti-tachycardia pacing pulses to terminate detected episodes of atrial tachycardia. Other devices are configured to predict the onset of atrial fibrillation, and deliver pacing pulses to prevent the atrial fibrillation from occurring. In particular, a device may be configured to detect premature atrial contractions (PACs) as trigger events that indicate the onset of atrial fibrillation. Delivery of pacing pulses in response to PAC detection can help prevent or decrease the occurrence of atrial fibrillation. Pacing pulses delivered in response to PAC detection are sometimes referred to as post-PAC pacing pulses.

SUMMARY

The invention is directed to identification of PACs that trigger arrhythmia. In particular, the invention involves analysis of PAC coupling interval, morphology or both to identify PACs that are more likely to trigger the onset of an arrhythmia episode. In this manner, the invention may be useful in avoiding unnecessary delivery of post-PAC pacing pulses, i.e., for detected PACs that are not likely to trigger arrhythmia. In addition, the invention may be useful in distinguishing different types of PACs to aid in diagnosis and formulation of pacing, drug, or other therapies.

In general, an implanted medical device stores a set of coupling interval and morphology criteria. The criteria may be developed during the course of a training period in which the implanted medical device detects numerous PACs, stores information relating to the coupling intervals and morphologies associated with the PACs, and detects whether the PACs actually trigger an arrhythmia episode. Based on the training period, the implanted medical device develops the criteria for comparison to subsequently detected PACs to identify PACs that trigger arrhythmia. Notably, the criteria may be unique for each individual patient. In this manner, the criteria may reflect the particular physical condition, disease state, and activity profile of the patient.

In response to the comparison, the implanted medical device determines whether to deliver post-PAC pacing in an attempt to prevent the arrhythmia, or take other actions such as initiating drug delivery. In each case, the implanted medical device can distinguish many PACs that are not likely to trigger arrhythmia, and thereby avoid unnecessary delivery of post-PAC therapies. The implanted medical device thereby reduces the number of post-PAC pacing pulses delivered to the patient, and the associated consumption of battery resources within the device. Accordingly, the invention may be helpful in avoiding unnecessary therapies and increasing device longevity.

In one embodiment, the invention provides an implantable medical device comprising a pulse generator to deliver pacing pulses to a chamber of the heart, and a processor to determine whether a sensed premature contraction is likely to trigger an arrhythmia, and control the pulse generator based on the determination.

In another embodiment, the invention provides a method comprising sensing a premature contraction within a chamber of a heart, determining whether the sensed premature contraction is likely to trigger an arrhythmia, and controlling delivery of pacing pulses based on the determination.

In an added embodiment, the invention provides a computer-readable medium comprising instructions to cause a processor to determine whether a sensed premature contraction is likely to trigger an arrhythmia, and control delivery of pacing pulses based on the determination.

In a further embodiment, the invention provides a method comprising sensing premature contractions over a period of time, identifying one or more characteristics of the premature contractions, determining whether the premature contractions trigger arrhythmia, and generating criteria associating the identified characteristics with a likelihood that premature contractions will trigger arrhythmia.

In another embodiment, the invention provides a method comprising sensing a premature contraction within a chamber of a heart, determining whether the sensed premature contraction is likely to trigger an arrhythmia, and selectively delivering therapy based on the determination. The therapy may include delivery of pacing pulses, drug delivery, or a surgical procedure

DETAILED DESCRIPTION

Figure 1:
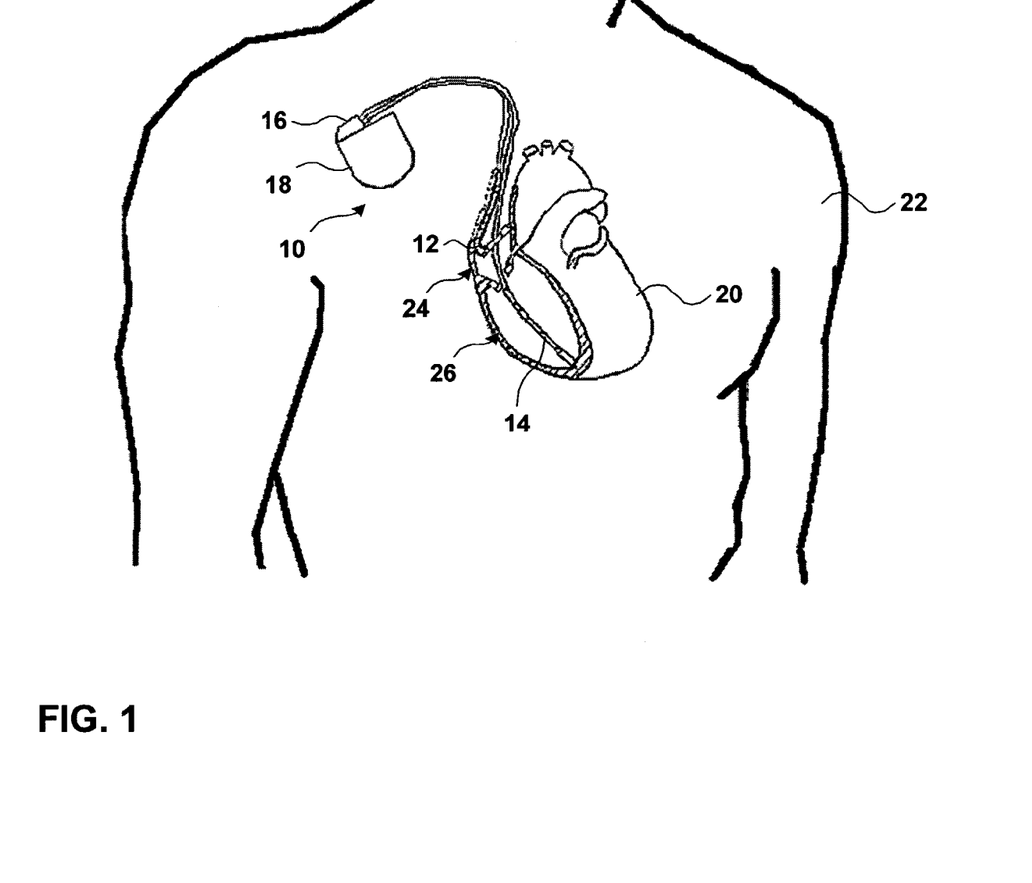
FIG. 1 is a schematic view of an exemplary medical device implanted within a human body.

FIG. 1 is a schematic view of an exemplary implantable medical device 10 implanted within a human patient 22. For purposes of illustration, this disclosure refers extensively to the detection and identification of premature atrial contractions. However, the invention may be applied to other premature contractions, such as premature ventricular contractions (PVCs). Accordingly, this disclosure should be considered limiting of the invention as broadly claimed and embodied herein.

IMD 10 identifies premature atrial contractions (PACs) that are likely to trigger arrhythmia. In particular, IMD 10 is capable of distinguishing PACs that are likely to trigger arrhythmia from PACs that are not likely to trigger arrhythmia. As will be described, IMD 10 analyzes a coupling interval or morphology, or both, associated with each PAC relative to predetermined criteria to determine whether the PAC can be classified as the type of PAC that triggers arrhythmia. The predetermined criteria may be developed as a result of a training period in which IMD 10 analyzes numerous PACs, and determines whether they appear to trigger arrhythmia episodes.

IMD 10 compares the criteria to coupling interval and morphology characteristics of subsequently detected PACs. In response to the comparison, IMD 10 determines whether to deliver post-PAC pacing in an attempt to prevent the arrhythmia, or take other actions such as initiating drug delivery. The drug delivery may be administered externally or via an implanted drug pump. In each case, IMD 10 is able to distinguish many PACs that are not likely to trigger arrhythmia, and thereby avoid unnecessary delivery of post-PAC therapies.

In the example of FIG. 1, IMD 10 is a pacemaker comprising atrial pacing and sensing lead 12 and ventricular pacing and sensing lead 14 attached to connector module 16 of hermetically sealed enclosure 18 and implanted near human or mammalian heart 20 of patient 22. Pacing and sensing leads 12 and 14 sense electrical signals attendant to the depolarization and depolarization of the heart 20, and further provide pacing pulses for causing depolarization of cardiac tissue in the vicinity of the distal ends thereof. Leads 12 and 14 may have unipolar or bipolar electrodes disposed thereon.

IMD 10 is one example of a device capable of practicing the invention in that IMD 10 has the capability of detecting PACs, and pacing the right atrium in response to the detected PAC in an attempt to prevent the onset of atrial fibrillation. In particular, atrial pacing and sensing lead 12 senses activation of the right atrium 24, and can deliver post-PAC pacing pulses to right atrium 24.

Ventricular pacing and sensing lead 14 senses activation of the right ventricle 26, and can pace right ventricle 26. IMD 10 is not the only implantable medical device that may practice the invention, however. The invention alternatively may be practiced by implantable medical devices that are configured to pace three or four chambers of heart 20, and that provide atrioventricular synchrony.

Figure 2:
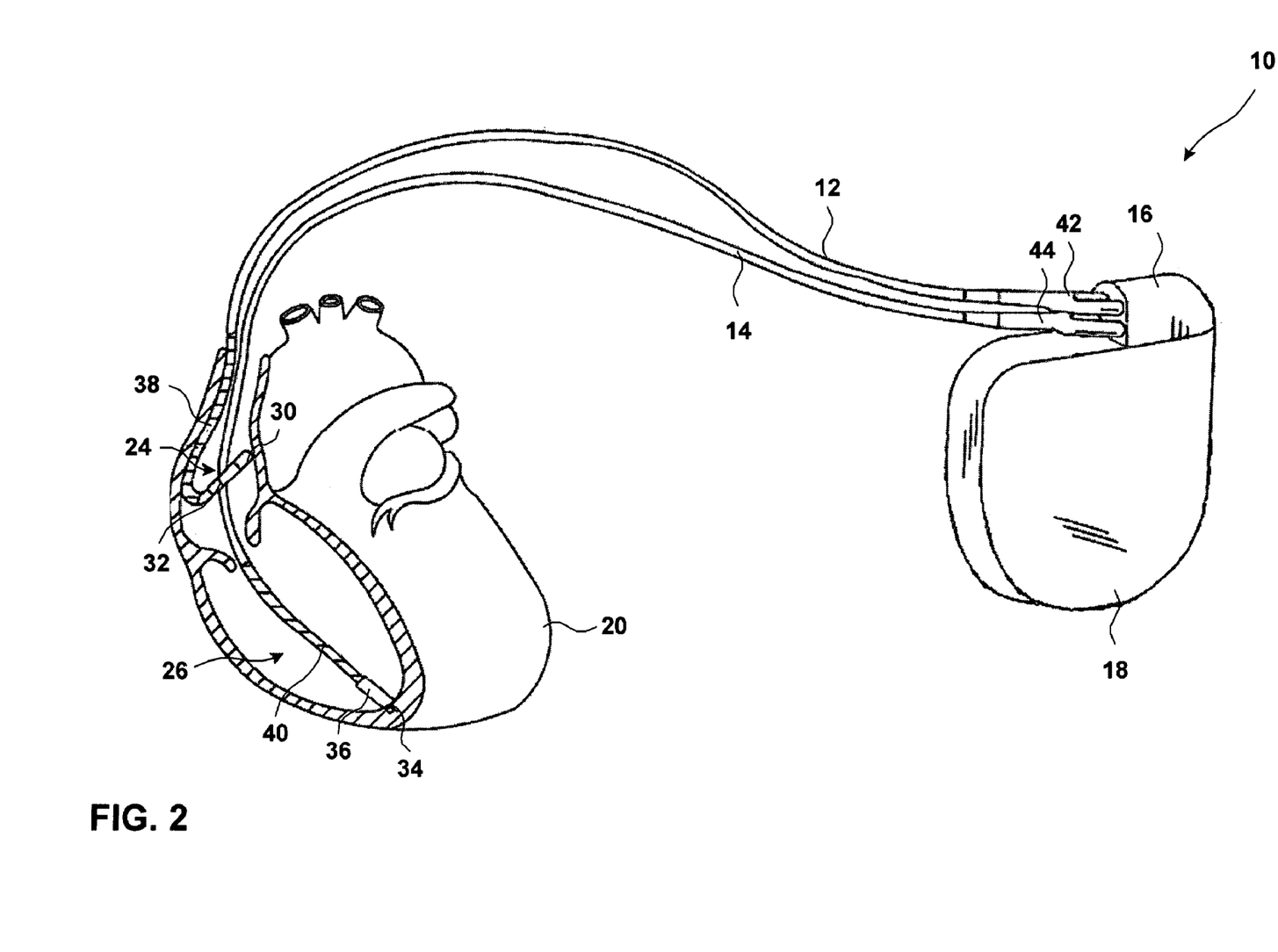
FIG. 2 is a diagram of the implantable medical device of FIG. 1 located in and near a heart.

FIG. 2 is a diagram of implantable medical device 10 of FIG. 1 located in and near heart 20. FIG. 2 shows IMD 10, with connector module 16 and hermetically sealed enclosure 18. Atrial and ventricular pacing leads 12 and 14 extend from connector module 16 to the right atrium 24 and right ventricle 26, respectively, of heart 20. Atrial electrodes 30 and 32 disposed at the distal end of atrial pacing lead 12 are located in right atrium 24. Ventricular electrodes 34 and 36 disposed at the distal end of ventricular pacing lead 14 are located in right ventricle 26.

A pulse generator (not shown in FIG. 2) inside enclosure 18 generate pacing pulses. The pacing pulses are delivered to right atrium 24 or right ventricle 26 by electrodes 30, 32, 34, 36. In accordance with the invention, a selected number of post-PAC pacing pulses are applied in a sequence to right atrium 24 to prevent atrial fibrillation. A processor (not shown in FIG. 2) in IMD 10 responds to detected PACs by directing delivery of post-PAC pacing pulses to prevent atrial fibrillation and thereby maintain effective hemodynamic function within heart 20.

In addition to pacing, IMD 10 may apply other forms of therapy. In FIG. 2, for example, atrial lead 12 and ventricular lead 14 include defibrillation electrodes 38 and 40, respectively. Defibrillation electrodes 38 and 40 deliver defibrillation shocks to right atrium 24 or right ventricle 26 when necessary to terminate an episode of atrial or ventricular defibrillation. Atrial and ventricular leads 12, 14 each include an elongated insulative lead body carrying one or more conductors insulatively separated from one another. At the proximal end of leads 12, 14 are bifurcated connectors 42, 44, which electrically couple the connectors to connector module 16 of IMD 10.

Figure 3:
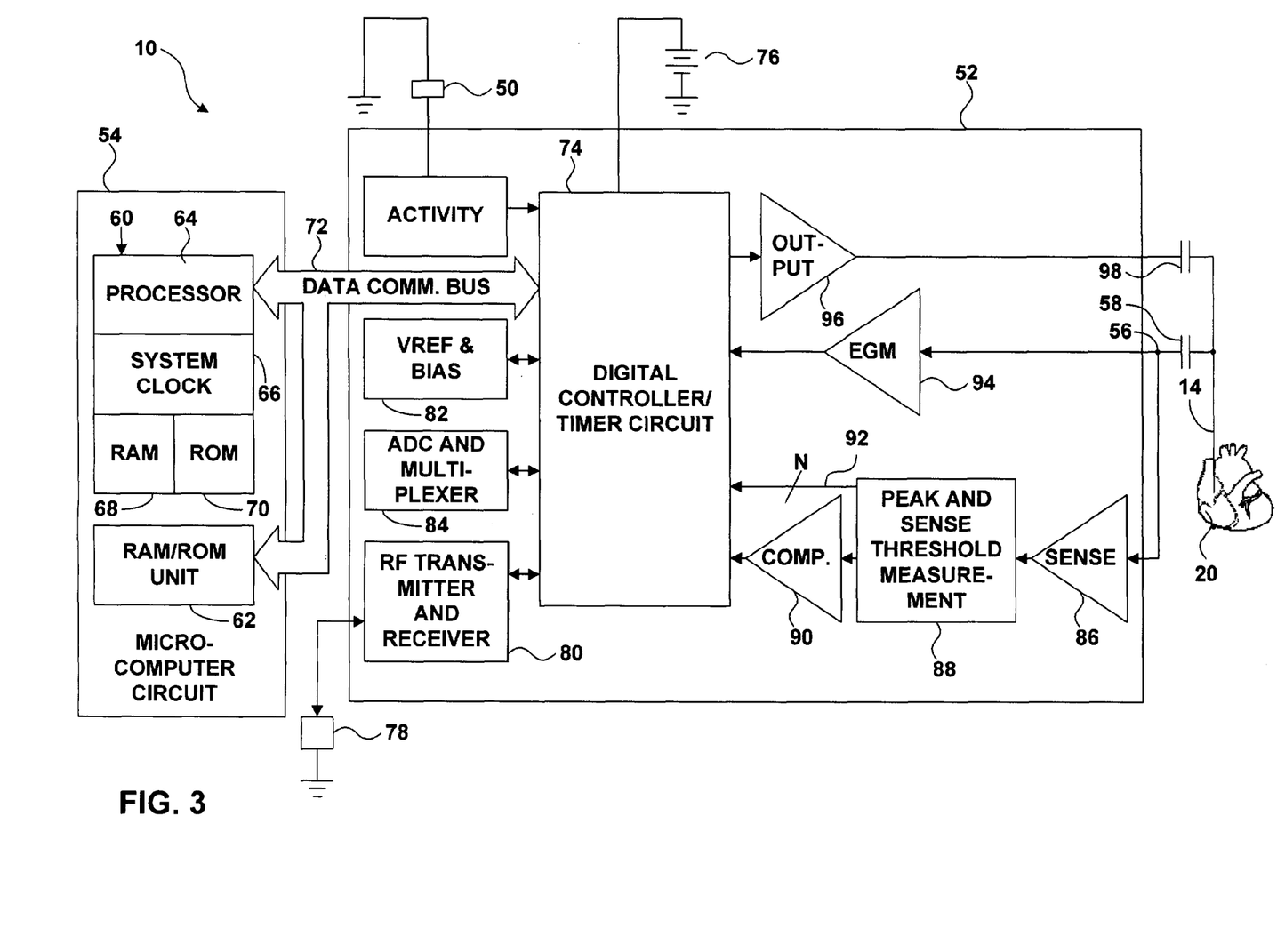
FIG. 3 is a block diagram illustrating the constituent components of the implantable medical device depicted in FIGS. 1 and 2.

FIG. 3 shows a block diagram illustrating exemplary components of IMD 10 in accordance with one embodiment of the invention, in which IMD 10 is a pacemaker having a microprocessor-based architecture. As shown in FIG. 3, IMD 10 may include one or more activity sensors 50. Activity sensor 50 may include an accelerometer, such as a piezoceramic accelerometer or a microelectromechanical accelerometer, that provides a sensor output that varies as a function of a measured parameter relating to a patient's metabolic requirements. In other words, activity sensor 50 detects motion of patient 22 that accompanies physical activity, and may adjust the pacing rate to the metabolic needs associated with the physical activity.

The output of activity sensor 50 is coupled to input/output circuit 52. Input/output circuit 52 contains analog circuits for interfacing with heart 20, activity sensor 50, and other components and circuits for the application of stimulating pulses to heart 20. For ease of illustration, IMD 10 in FIG. 3 is shown with only lead 14 connected. Similar circuitry and connections not explicitly shown in FIG. 3 apply to lead 12 (shown in FIGS. 1 and 2), however. Lead 14 is coupled to node 56 in IMD 10 through input capacitor 58.

The rate of heart 20 is controlled by software-implemented algorithms stored within microcomputer circuit 54. In the example of FIG. 3, microcomputer circuit 54 comprises on-board circuit 60 and off-board circuit 62. On-board circuit 60 may include processor 64, system clock circuit 66 and on-board random access memory (RAM) 68 and read-only memory (ROM) 70. Processor 64 may take the form of a microprocessor, digital signal processor (DSP), ASIC, FPGA, or other integrated or discrete logic circuitry capable of performing the functions described herein. Off-board circuit 62 comprises a RAM/ROM unit. On-board circuit 60 and off-board circuit 62 are each coupled by data communication bus 72 to digital controller/timer circuit 74. Microcomputer circuit 54 may comprise a custom integrated circuit device augmented by standard RAM/ROM components.

Microcomputer circuit 54 directs delivery of post-PAC paces in response to a detected PAC to prevent atrial fibrillation and thereby maintain hemodynamic performance. In accordance with the invention, IMD 10 detects premature atrial contractions (PACs), and determines whether to deliver post-PAC pacing pulses to prevent atrial fibrillation. In particular, IMD 10 is configured to identify PACs that trigger arrhythmia. If IMD 10 determines that a detected PAC is not likely to trigger arrhythmia, the IMD does not deliver post-PAC pacing pulses. If the detected PAC is likely to trigger arrhythmia, however, IMD 10 delivers post-PAC pacing pulses. Either arrangement, whether based on a microprocessor or dedicated circuitry, will generally be referred to herein as a processor that determines whether a sensed premature contraction is likely to trigger an arrhythmia, and controls the pulse generator based on the determination.

Processor 64 of IMD 10 analyzes the detected PACs to determine whether each PAC is likely to trigger arrhythmia. For example, processor 64 may analyze the PAC coupling interval, and classify the PAC as likely or unlikely to cause arrhythmia based on the length of the coupling interval. In general, the coupling interval refers to the length of time between the PAC and the preceding normal contraction. If the coupling interval falls in a range that is indicative of arrhythmia triggering, processor 64 controls digital controller/timer circuit 74 to deliver a sequence of post-PAC pacing pulses. In some embodiments, a dedicated detector circuit, either integrated or discrete, may be provided to perform the function of identifying triggering PACs based on coupling interval or morphology. Processor 64 may be more desirable, however, in terms of processing power and programming flexibility.

As an alternative, processor 64 may analyze one or more morphology characteristics of the detected PAC to identify PACs that are more likely to trigger arrhythmia. In this manner, the invention may be useful in avoiding unnecessary delivery of post-PAC pacing pulses, i.e., for detected PACs that are not likely to trigger arrhythmia. In addition, the invention may be useful in distinguishing different types of PACs to aid in diagnosis and formulation of pacing, drug, or other therapies.

In general, microcomputer circuit 54 stores data defining a set of coupling interval criteria, morphology criteria, or both that aid in distinguishing PACs that trigger arrhythmia from PACs that do not. Specific premature atrial contractions (PACs) can be a trigger for atrial arrhythmias, especially PACs originating from the pulmonary vein ostia. These triggering PACs may be identified based on the PAC coupling intervals, the morphology of the PACs or both, and thereby distinguished from non-triggering PACs. In some cases, identification of the triggering PACs may permit a physician to assess the origin of the PACs and thereby select surgical procedures, such as ablation, to prevent the occurrence or propagation of the PACs.

The criteria may be developed during the course of a training period in which the IMD 10 detects numerous PACs, stores information relating to the coupling intervals, morphologies, or both, associated with the PACs, and detects whether the PACs actually trigger an arrhythmia episode. Based on the training period, IMD 10 develops the criteria for comparison to subsequently detected PACs to identify PACs that trigger arrhythmia. IMD 10 performs the training period following implant and, consequently, the criteria may be unique for each individual patient 11. In this manner, the criteria may reflect the particular physical condition, disease state, and activity profile of the patient 11.

In operation, following the training period, IMD 10 detects PACs and identifies characteristics of the PACs such as coupling interval, morphology or both. IMD 10 then compares the characteristics to the predetermined criteria obtained from the training period. In response to the comparison, IMD 10 determines whether to deliver post-PAC pacing in an attempt to prevent the arrhythmia, or take other actions such as initiating drug delivery. In each case, IMD 10 can distinguish many PACs that are not likely to trigger arrhythmia, and thereby avoid unnecessary delivery of post-PAC therapies.

Electrical components shown in FIG. 3 are powered by an appropriate implantable battery power source 76. For ease of illustration, the coupling of battery power to the various components of IMD 10 is not shown in FIG. 3. IMD 10 reduces the number of post-PAC pacing pulses delivered to the patient, and the associated consumption of battery resources provided by batter power source 76. Accordingly, IMD 10 may be effective in avoiding unnecessary therapies and increasing device longevity.

Antenna 78 is connected to input/output circuit 52 to permit uplink/downlink telemetry through radio frequency (RF) transmitter and receiver telemetry unit 80. IMD 10 in FIG. 3 is programmable by an external programmer (not shown) that communicates with IMD 10 via antenna 78 and RF transmitter and receiver telemetry unit 80.

In some embodiments, an external programming unit can be used to cause IMD 10 to enter a training period in which the IMD detects numerous PACs, stores characteristics for the PACs, such as coupling interval and morphology, and stores an indication as to whether the individual PACs caused, i.e., triggered, arrhythmias. At the end of the training period, or during the course of the training period, IMD 10 processes the stored characteristics and triggering indications to generate a set of triggering criteria. The triggering criteria specify ranges of PAC characteristics such as Coupling interval or morphological characteristics observed to trigger arrhythmia on a substantially regular basis.

VREF and Bias circuit 82 generates stable voltage reference and bias currents for analog circuits included in input/output circuit 52. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are transmitted from processor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 52.

Digital controller/timer circuit 74 is coupled to sensing circuitry, including sense amplifier 86, peak sense and threshold measurement unit 88 and comparator/threshold detector 90. Sense amplifier 86 amplifies electrical cardiac signals sensed via lead 14 and provides an amplified signal to peak sense and threshold measurement circuitry 88, which in turn provides an indication of peak sensed voltages and measured sense amplifier threshold voltages on multiple conductor signal path 92 to digital controller/timer circuit 74. An amplified sense amplifier signal is also provided to comparator/threshold detector 90.

Digital controller/timer circuit 74 is further coupled to electrogram (EGM) amplifier 94 for receiving amplified and processed signals sensed by lead 14. The electrogram signal provided by EGM amplifier 94 is employed, for example, when IMD 10 is being interrogated by an external programmer to transmit a representation of a cardiac analog electrogram. Output pulse generator 96 provides pacing stimuli to heart 20 through coupling capacitor 98 in response to a pacing trigger signal provided by digital controller/timer circuit 74.

IMD 10 may sense the P-waves, i.e., atrial depolarizations, via lead 12, sense amplifier 86, peak sense and threshold measurement unit 88 and comparator/threshold detector 90. The time interval of the P-wave relative to a previous P-wave, i.e., the coupling interval, can be used both to detect PACs and to distinguish arrhythmia triggering PACs from non-triggering PACs. Again, triggering PACs are those PACs determined to be likely to cause an episode of arrhythmia.

Consequently, sense amplifier 86, peak sense and threshold measurement unit 88 and comparator/threshold detector 90 are configured to serve as PAC detector. In response to PAC detection, processor 64 directs digital controller/timer circuit 74 to deliver a sequence of post-PAC pacing pulses, or prevent delivery of post-PAC, pacing pulses, depending on the analysis of the PAC relative to the stored triggering criteria by processor 64. When a triggering PAC is identified, the number of pulses in the post-PAC sequence and the post-PAC pacing interval also may be determined by processor 64, which then drives digital controller/timer circuit 74 to deliver the post-PAC pacing pulses.

In general, IMD 10 compares the coupling interval of a detected PAC to a coupling interval range indicative of arrhythmia triggering PACs. Again, the coupling interval range may form part of triggering criteria generated by IMD 10 following a training period in which the IMD analyzes numerous PACs for triggering of associated arrhythmia episodes. The coupling interval range associated with PACs that trigger arrhythmia may vary on a patient-by-patient basis, e.g., as a function of particular physical condition, disease state, and activity profile of the patient.

Accordingly, IMD 10 may establish a unique coupling interval range for the patient in which the IMD is implanted. Following the training period, IMD 10 determines the coupling interval of each detected PAC and compares the coupling interval to the coupling interval range established for the patient. If the coupling interval falls in the coupling interval range, IMD 10 interprets the detected PAC to be a triggering PAC, and delivers post-PAC pacing pulses to the right atrium. If the detected PAC is not a triggering PAC, IMD 10 refrains from delivery of post-PAC pacing pulses.

As an alternative, IMD 10 analyzes one or more morphology characteristics of the detected PACs to identify PACs that are likely to trigger arrhythmia. Examples of morphology characteristics that may used to distinguish triggering including any of the following: minimum voltage of the PAC waveform, maximum voltage of the PAC waveform, time of maximum voltage from the start of the PAC waveform, time of minimum voltage of the PAC waveform, maximum slope of the PAC waveform, time of maximum slope of the PAC waveform from the start of the PAC waveform, minimum slope of the PAC waveform, time of minimum slope of the PAC waveform from the start of the PAC waveform, and PAC width, i.e, time between first and last amplitude threshold crossings of the PAC waveform. Each of the above morphology characteristics may be analyzed within a filtered or unfiltered signal representing the detected PAC. Such morphology characteristics may be efficiently processed, identified and compared using digital signal analysis. In this case, processor 64 may take the form of a digital signal processor.

One or more of the above morphology characteristics may be observed as a characteristic of a PAC that is more likely to trigger arrhythmia. The significance of the individual characteristics, as well as the effect of the particular value ranges of the characteristics, in triggering arrhythmia may vary from patient-to-patient. Accordingly, IMD 10 may be configured to IMD 10 establish unique ranges for the characteristics as a result of a training period. In the training period, IMD 10 detects numerous PACs, processes and stores morphological characteristics for the PACs, such as minimum and maximum voltage, slope, and the like, and stores an indication as to whether the individual PACs caused, i.e., triggered, arrhythmias. On the basis of the stored data, IMD 10 generates morphology characteristic criteria to distinguish triggering PACs from non-triggering PACs, and stores the criteria. IMD 10 thereafter compares one or more morphology characteristics of newly detected PACs to the stored criteria to determine whether the newly detected PACs are likely to trigger arrhythmia. If so, IMD 10 delivers post-PAC pacing pulses to the right atrium. If the detected PAC is not a triggering PAC, IMD 10 refrains from delivery of post-PAC pacing pulses.

As described herein, IMD 10 may identify triggering PACs based on the coupling interval or one or more morphology characteristics associated with the PAC. In some embodiments, however, IMD 10 analyzes both coupling interval and morphology characteristics in order to identify triggering PACs with heightened confidence. For exampled, IMD 10 may be configured to deliver post-PAC pacing pulses only if both the coupling interval and morphology characteristics satisfy the applicable criteria. In this case, IMD 10 is biased toward not applying post-PAC pacing pulses unless a PAC can be confidently identified as a triggering PAC. Alternatively, IMD 10 may be configured to prevent delivery of post-PAC pacing pulses only if both the coupling interval and morphology characteristics do not satisfy the applicable criteria. In this case, IMD 10 is biased toward applying post-PAC pacing pulses unless a PAC can be confidently identified as a non-triggering PAC.

Figure 4:
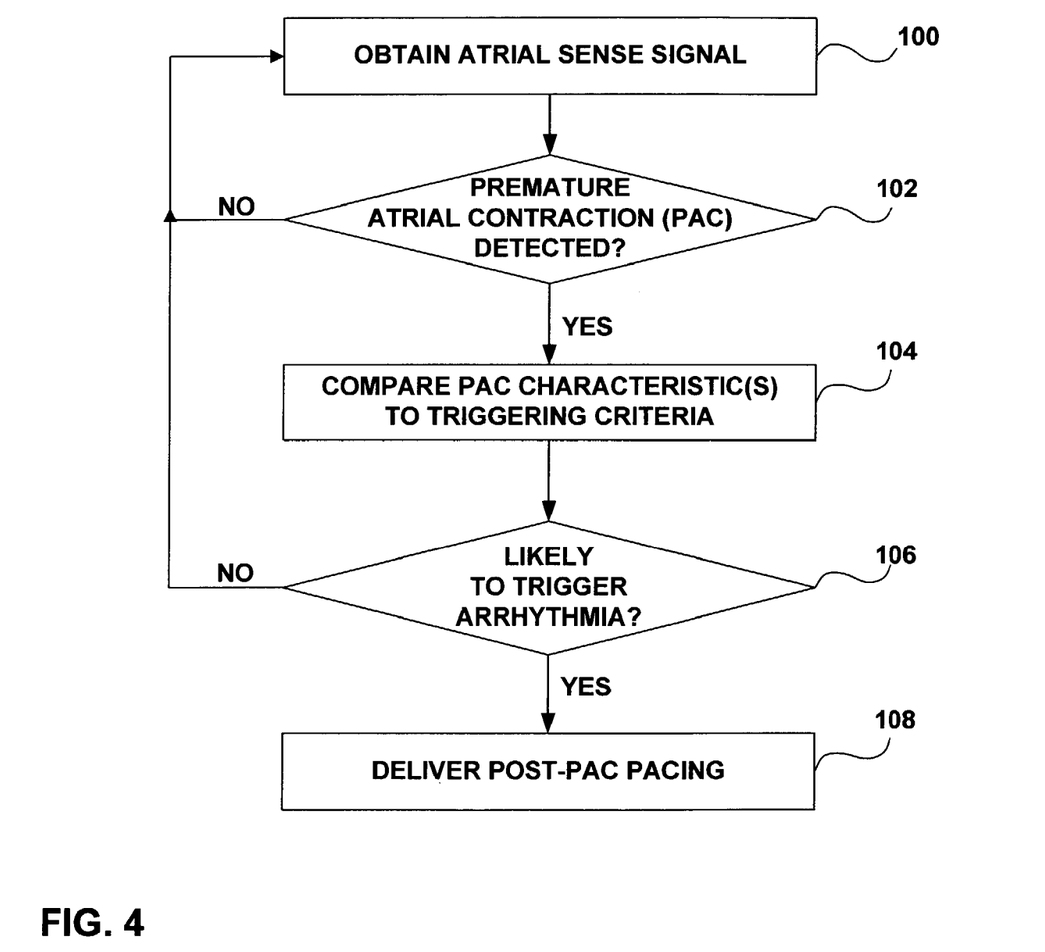
FIG. 4 is a flow diagram illustrating a technique for identification of PACs that trigger arrhythmia.

FIG. 4 is a flow diagram illustrating a technique for identification of PACs that trigger arrhythmia. As shown in FIG. 4, IMD, 10 obtains an atrial sense signal (100) and determines whether a PAC is detected (102). If not, IMD 10 continues to obtain atrial sense signals (100). If the atrial sense signal indicates a PAC (102), IMD 10 compares one or more characteristics of the PAC to predetermined triggering criteria (104). If the PAC satisfies the criteria, IMD 10 identifies the PAC as being likely to trigger arrhythmia (106). If the PAC does not satisfy the criteria, IMD 10 continues to obtain the atrial sense signals (100). If IMD 10 identifies the PAC as being likely to trigger arrhythmia, the IMD delivers post-PAC pacing pulses to the heart in an attempt to prevent the arrhythmia from occurring (108).

Figure 5:
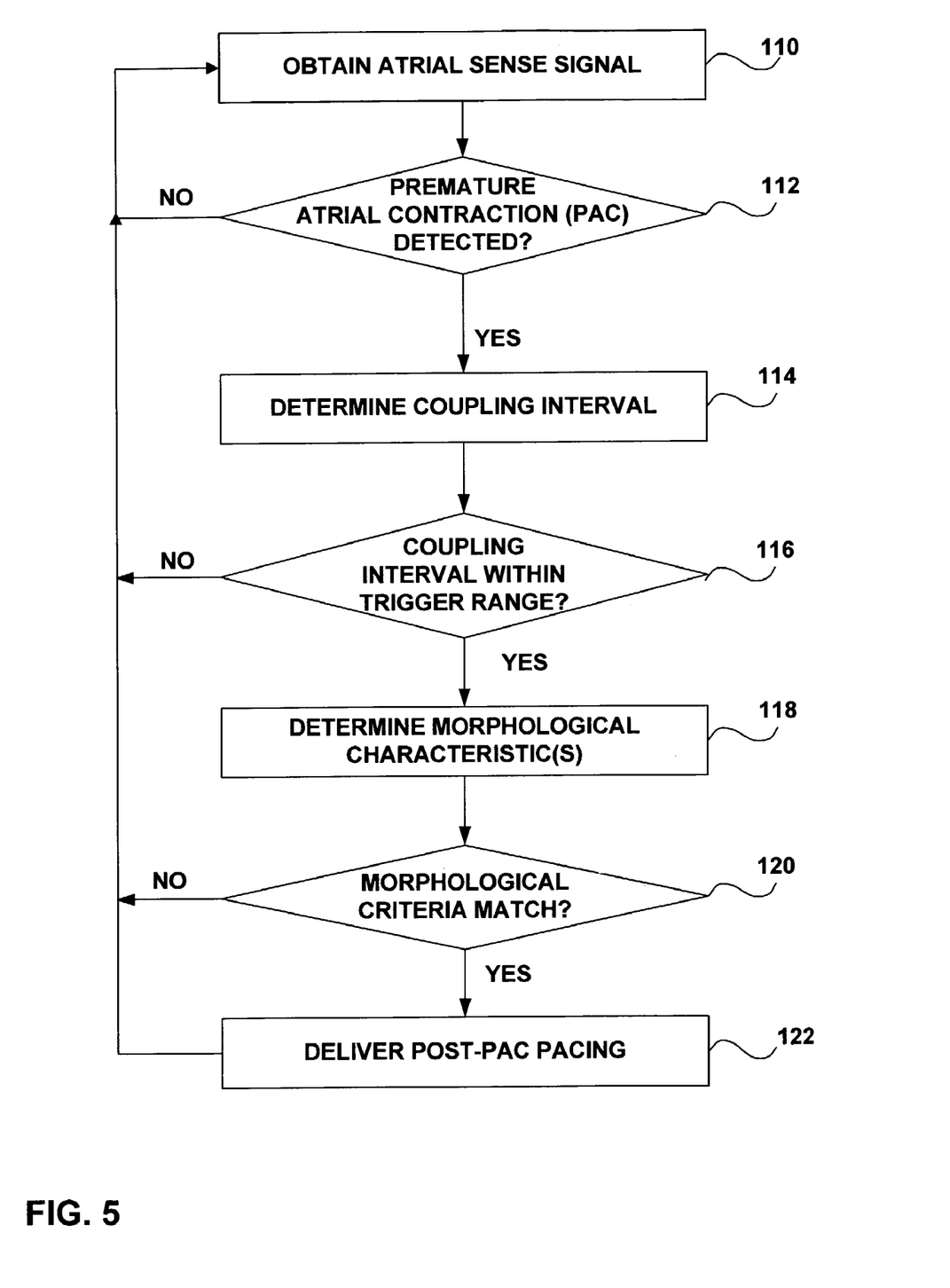
FIG. 5 is a flow diagram illustrating the technique of FIG. 4 in greater detail.

FIG. 5 is a flow diagram illustrating the technique of FIG. 4 in greater detail. In the example of FIG. 5, IMD 10 considers both coupling interval and morphological characteristics in identifying triggering PACs. In other embodiments, however, IMD 10 may consider either coupling interval or morphological characteristics individually. As shown in FIG. 5, IMD 10 obtains an atrial sense signal (110), and detects whether the signal indicates a PAC (112). If so, IMD 10 determines the coupling interval of the detected PAC (114), and compares the coupling interval to trigger range criteria (116). Again, the trigger range criteria may be a predetermined range of coupling intervals considered to be indicative of a PAC that is likely to trigger arrhythmia. If the coupling interval does not satisfy the triggering range criteria, IMD 10 disregards the PAC and continues to obtain atrial sense signals (110) for PAC detection.

If the coupling interval of the detected PAC satisfies the trigger range criteria (116), IMD 10 proceeds to determine one or more morphological characteristics associated with the detected PAC (118). In some embodiments, contrary to the example of FIG. 5, the analysis of morphological characteristics may precede the coupling interval analysis. If the one or more morphological characteristics considered by IMD 10 matches the applicable criteria (120), the IMD deliver post-PAC pacing pulses in an attempt to prevent the onset of arrhythmia with the patient's heart (122). IMD 10 also may use the criteria to identify triggering PACs, and thereby determine whether to control other therapies such as drug delivery.

Figure 6:
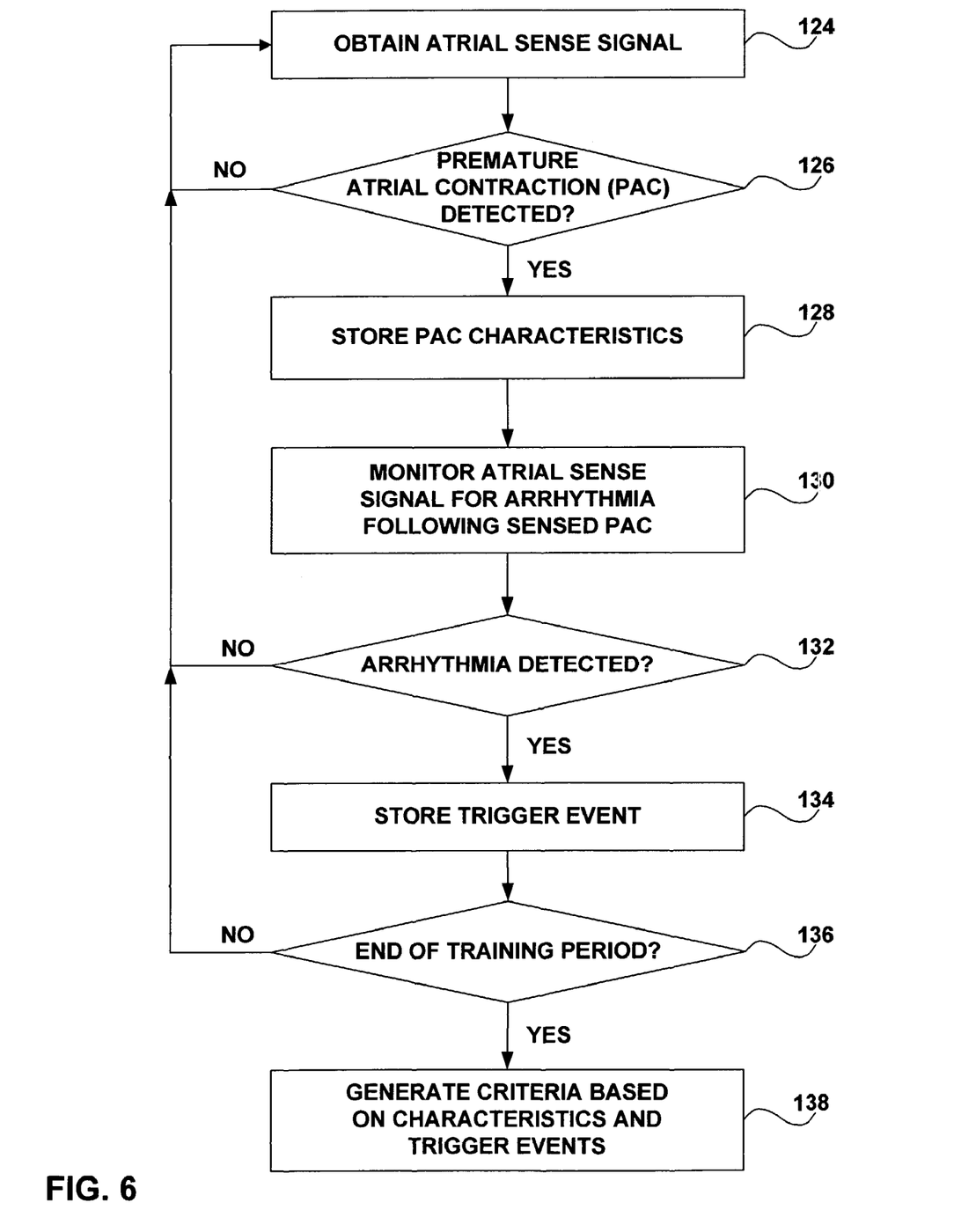
FIG. 6 is a flow diagram illustrating collection of PAC information in the course of a training period to develop criteria for identification of PACs that trigger arrhythmia.

FIG. 6 is a flow diagram illustrating collection of PAC information in the course of a training period to develop criteria for identification of PACs that trigger arrhythmia. As shown in FIG. 6, IMD 10 obtains the atrial sense signal (124), and detects the presence of a PAC (126). If a PAC is detected, IMD 10 stores one or more characteristics associated with the PAC (128), such as coupling interval, morphological characteristics, or both. IMD 10 then monitors the atrial sense signal to determine whether the sensed PAC triggers an arrhythmia (130). If so, IMD detects an arrhythmia (132) and stores a trigger event (134) to indicate that the particular observed PAC characteristics were associated with a triggering PAC, i.e., a PAC that was observed to trigger an arrhythmia.

IMD 10 continues to detect numerous PACs over an extended period of time, e.g., several days or weeks. At the end of the training period (136), IMD 10 processes the stored data to generate criteria based on the stored characteristics and trigger events (138). Alternatively, IMD 10 may generate the criteria during the course of the training period and update the criteria as new triggering PACs are observed. As a further alternative, following the completion of the training period, the criteria need not be static. Instead, IMD 10 may continue to update the criteria when it detects triggering PACs that did not previously satisfy the criteria for delivery of post-PAC pacing. In any event, IMD 10 thereafter employs the criteria to detected PACs to more discriminately apply post-PAC pacing. Also, the criteria and process described in FIG. 6 may be employed to determine whether to deliver other therapies to prevent arrhythmia, such as drug delivery. Although illustrated for purposes of example in reference to a training period, the techniques may be implemented in an adaptive fashion to continuously update the triggering criteria stored by IMD 10. In other words, the triggering criteria may be updated concurrent with the delivery of therapy to the patient.

Many embodiments of the invention have been described. Various modifications may be made without departing from the scope of the claims. For example, the invention is not limited to the particular implantable medical devices described above, but may be practiced by a wide variety of implantable medical devices. In particular, as mentioned previously, the invention is not necessarily limited to PACs, but may be used in conjunction with other premature contractions, such as premature ventricular contractions (PVCs). As a further variation, the invention may be used to identify and distinguish different types of triggering PACs in order to make assessments as to the origins of the PACs, and thereby better inform a physician for selection of surgical procedures such as ablation to alleviate the sources of the PACs.

In addition, the invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

These and other embodiments are within the scope of the following claims.

What is claimed is:

1. An implantable medical device comprising:
   an electrode adapted for implantation relative to a chamber of the heart for sensing cardiac signals;
   a pulse generator, coupled to the electrode, to deliver pacing pulses to a chamber of the heart; and
   a processor for receiving the cardiac signals sensed by the electrode and to discriminate between a sensed cardiac signal being an arrhythmia triggering type premature contraction and a sensed cardiac signal being a non-arrhythmia triggering type premature contraction, and to selectively control the pulse generator based on the determination of the type of sensed cardiac signal, the processor comprising means for performing the following functions:
   identifying signals indicative of premature contractions within a chamber of a heart;
   determining whether arrhythmias follow the sensed signals indicative of premature contractions;
   using the sensed signals indicative of premature contractions and the following arrhythmias to define criteria indicative of whether a subsequent sensed signal indicative of a premature contraction is an arrhythmia triggering type and storing the criteria in the pacemaker;
   identifying a subsequent signal indicative of a premature contraction within the chamber of the heart;
   determining whether the subsequent signal indicative of a premature contraction is an arrhythmia triggering type premature contraction or a non-arrhythmia triggering type premature contraction; and
   controlling delivery of pacing pulses by the pulse generator based on the determination.

2. The device of claim 1, further comprising an implantable cardiac lead carrying the sense electrode to sense the premature contraction within the chamber of the heart.

3. The device of claim 1, wherein the processor controls the pulse generator to deliver the pacing pulses when the processor determines that the sensed cardiac signal correspond to the arrhythmia triggering type premature contraction and controls the pulse generator to prevent delivery of the pacing pulses when the processor determines that the sensed cardiac signal corresponds to the non-arrhythmia triggering types premature contraction is not likely to trigger an arrhythmia.

4. The device of claim 1, wherein the processor discriminates based on a coupling interval associated with the premature contraction.

5. The device of claim 1, further comprising a memory storing a set of criteria, wherein the processor discriminates by comparing the premature contraction to the stored criteria.

6. The device of claim 1, wherein the premature contraction is a premature atrial contraction, the device further comprising an implantable atrial lead carrying a sense electrode to sense the premature atrial contraction.

7. A method comprising:
   using a pacemaker to sense premature contractions within a chamber of a heart;
   using the pacemaker to sense whether arrhythmias follow the sensed premature contractions;
   using the sensed premature contractions and the following sensed arrhythmias to define criteria indicative of whether a subsequent sensed premature contraction is an arrhythmia triggering type and storing the criteria in the pacemaker;
   using the pacemaker, sensing a subsequent premature contraction within the chamber of the heart;
   determining whether the sensed subsequent premature contraction is an arrhythmia triggering type premature contraction or a non-arrhythmia triggering type premature contraction; and
   controlling delivery of pacing pulses by the pacemaker based on the determination.

8. The method of claim 7, further comprising sensing the premature contraction via a sense electrode carried by a lead implanted within the heart.

9. The method of claim 7, further comprising delivering the pacing pulses when the determination indicates that the premature contraction is an arrhythmia triggering type premature contraction, and preventing delivery of the pacing pulses when the determination indicates that the premature contraction is a non-arrhythmia triggering type premature contraction.

10. The method of claim 7, wherein determining is based on a coupling interval associated with the premature contraction.

11. The method of claim 7, further comprising storing a set of criteria in a memory associated with an implanted medical device and determining further comprises comparing the premature contraction to the stored criteria.

12. The method of claim 7, wherein the premature contraction is a premature atrial contraction, the method further comprising sensing the premature atrial contraction via an implanted atrial lead carrying a sense electrode.

\* \* \* \* \*